United States Patent
Hart et al.

[11] Patent Number: 5,814,059
[45] Date of Patent: Sep. 29, 1998

[54] VEIN-BRANCH ACCESSING DEVICE

[75] Inventors: Charles C. Hart, Huntington Beach; Eric Lee, Irvine, both of Calif.

[73] Assignee: Applied Medical Resources Corporation, Laguna Hills, Calif.

[21] Appl. No.: 780,982

[22] Filed: Jan. 8, 1997

[51] Int. Cl.$^6$ .......................... A61B 17/00; A61B 17/22; A61B 17/32; A61B 17/10

[52] U.S. Cl. .......................... 606/190; 606/159; 606/167; 606/142

[58] Field of Search ................................ 606/1, 142–144, 606/159, 167, 170, 171, 190–200

[56] References Cited

U.S. PATENT DOCUMENTS

| | | | |
|---|---|---|---|
| 5,439,470 | 8/1995 | Li | 606/148 |
| 5,472,438 | 12/1995 | Schmit et al. | 606/1 |
| 5,472,446 | 12/1995 | Torre | 606/148 |
| 5,603,720 | 2/1997 | Kieturakis | 606/191 |

*Primary Examiner*—Glenn K. Dawson
*Attorney, Agent, or Firm*—Richard L. Myers

[57] ABSTRACT

A vein-branch accessing device includes at least one probe adapted for contacting a surface of a vein of the patient. The probe is further adapted for moving along the surface of the vein, to thereby guide the vein-branch accessing device over the surface of the vein and along the length of the vein, beneath the skin. The vein-branch accessing device further includes a vein branch indicator, which is adapted for indicating to an operator of the vein-branch accessing device that the probe has moved along the surface of the vein to a vein branch. The vein-branch accessing device further includes accessing structure, which is adapted for facilitating access to the vein branch. The accessing structure may include a port, which is adapted for accommodating either a clip or a clip applier therethrough. The clip is adapted for fitting around and occluding the vein branch, and the clip applier is adapted for severing the vein branch from the vein. The probe includes a vein bed separator having a shovel-shaped blade at an end thereof.

65 Claims, 4 Drawing Sheets

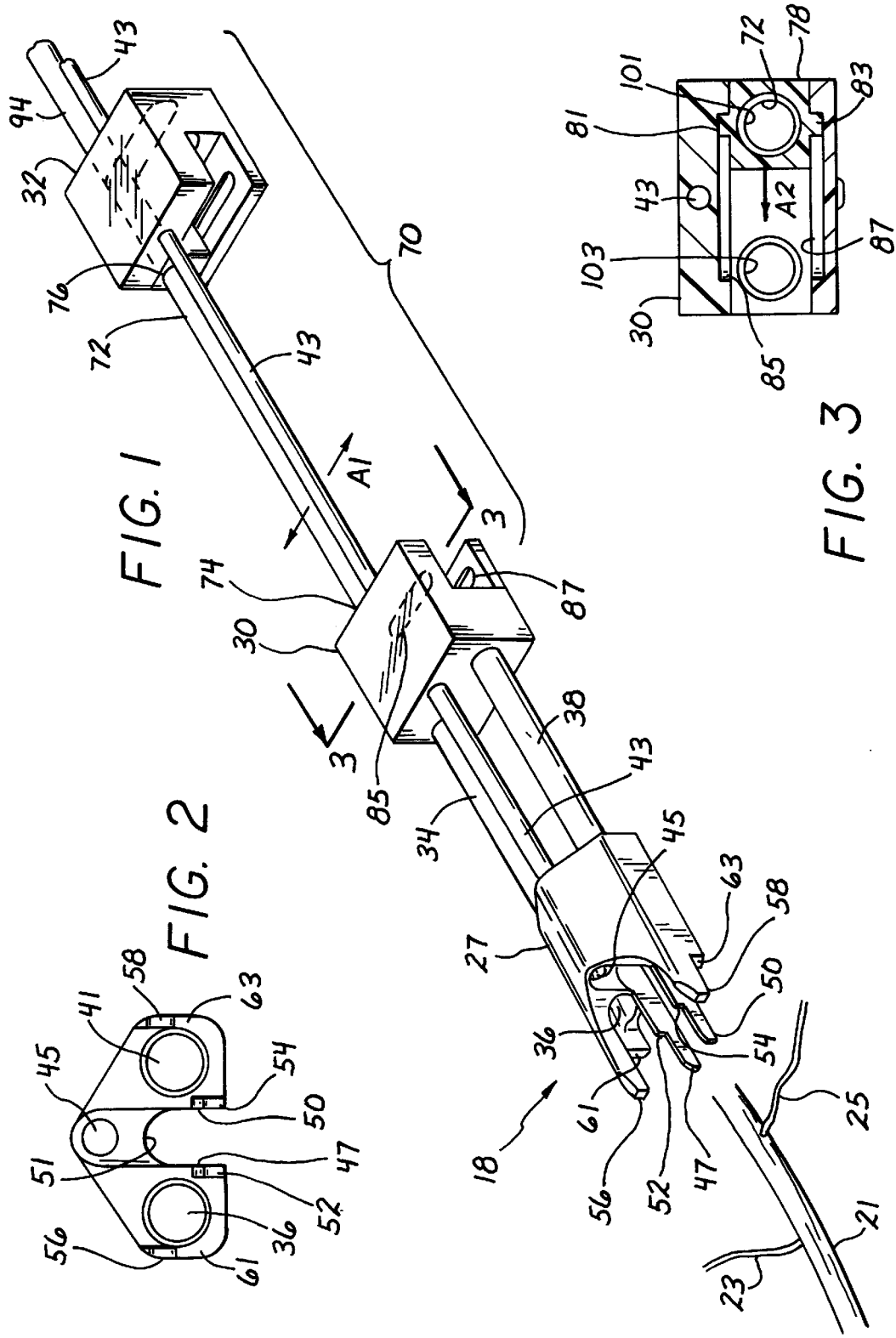

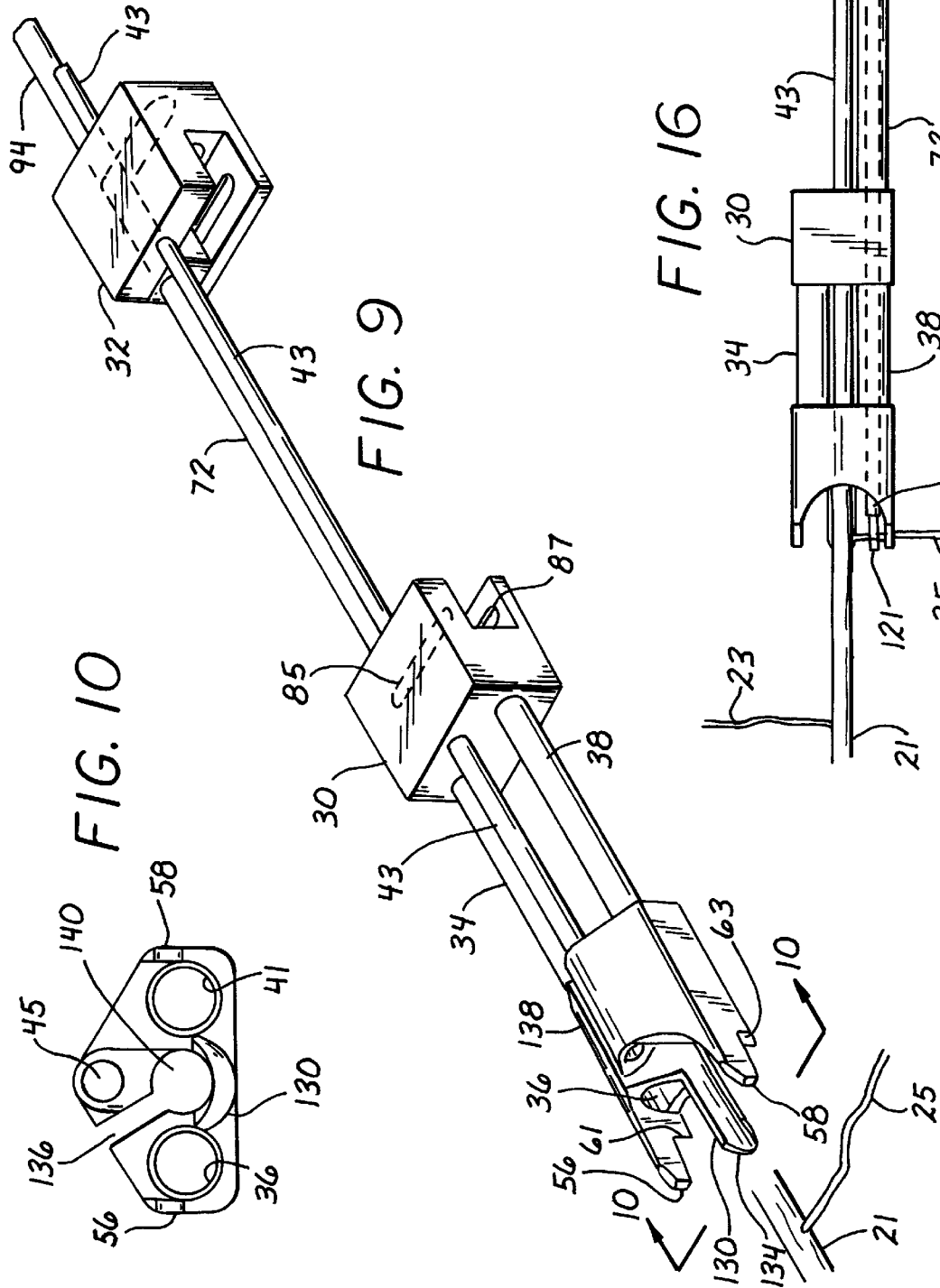

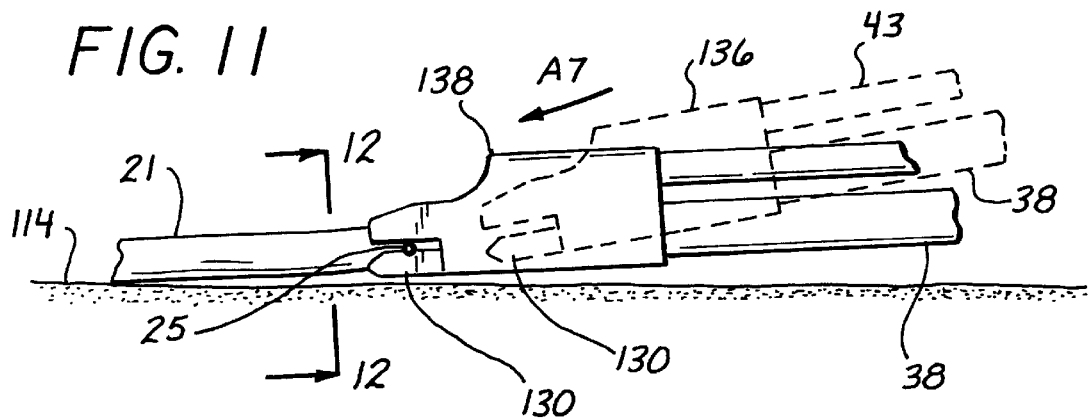
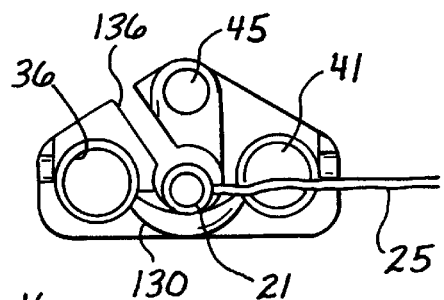
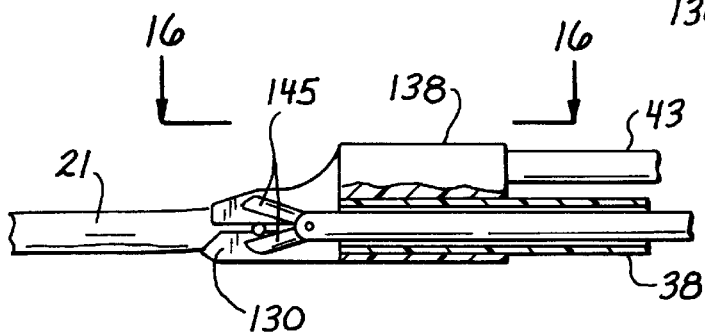
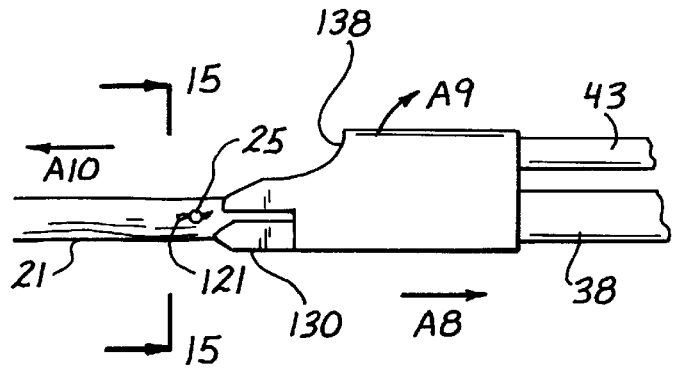
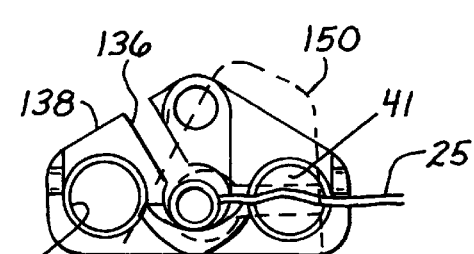

VEIN-BRANCH ACCESSING DEVICE

BACKGROUND OF THE INVENTION

1. Field of the Invention

The present invention relates generally to vein processing devices and, more particularly, to a vein-branch accessing device for occluding or severing side branches of a vein.

2. Description of Related Art

The term "saphena" denotes either of two main superficial veins of the human leg, one larger than the other, that begin at the foot. The larger saphenous vein is subject to two common medical procedures. In a first medical procedure, the larger saphenous vein is harvested from the leg of the patient and used as a bypass, for example, in another area of the body of the patient. Harvesting of the saphenous vein involves occluding each of the side branches of the saphenous vein and, subsequently, severing these side branches from the saphenous vein, before removing the saphenous vein from the leg of the patient.

In a second medical procedure, the saphenous vein is left within the leg of the patient, but is converted into an artery. This second medical procedure may be applicable, for example, when a patient's feet do not receive an adequate blood supply. In many instances, one or more of the one-way diotic valves of the saphenous vein that facilitate blood flow back to the heart of the patient are disrupted in this procedure, to thereby allow for blood flow in a direction from the saphenous vein into the side branches of the saphenous vein. The two ends of the saphenous vein are then connected to arteries, resulting in a flow of blood through the saphenous vein to the feet of the patient. This conversion process is performed in-situ, and typically involves occluding, rather than severing, the side branches of the saphenous vein to thereby facilitate a maximum flow of blood to the foot of the patient.

The two above-described medical procedures typically require a long incision along a length of the leg of the patient, corresponding to the length of the saphenous vein. Such an incision is obviously undesirable for several reasons, including increased susceptibility to infection, scarring, and increased trauma to the patient. A need exists in the prior art for an apparatus and method for performing medical procedures on the saphenous vein, without requiring a long incision along the length of the patient's leg.

SUMMARY OF THE INVENTION

The vein-branch harvesting device of the present invention is adapted for performing operations on the saphenous vein, beneath the skin. Since the vein-branch harvesting device can be inserted through a small incision or puncture, the vein-branch harvesting device of the present invention does not require a longitudinal incision along the length of the patient's leg.

The vein-branch accessing device of the present invention includes at least one probe adapted for contacting a surface of a vein of the patient. The probe is further adapted for moving along the surface of the vein, to thereby guide the vein-branch accessing device over the surface of the vein and along the length of the vein, beneath the skin. The vein-branch accessing device further includes a vein branch indicator, which is adapted for indicating to an operator of the vein-branch accessing device that the probe has moved along the surface of the vein to a vein branch. The vein-branch accessing device further includes accessing means, which are adapted for facilitating access to the vein branch.

The accessing means may include a port, which is adapted for accommodating either a clip or a clipper therethrough. The clip is adapted for fitting around and occluding the vein branch, and the clipper is adapted for severing the vein branch from the vein. The probe includes a vein bed separator having a shovel-shaped blade at an end thereof.

The vein-branch indicator may include a scope for providing a visual aid to the operator. The vein-branch indicator may also include a transverse surface, which is disposed on the probe and which is generally transverse to an axis of the vein branch.

According to one aspect of the present invention, a vein-branch accessing device is provided for being inserted through an incision of the skin of the patient and for being moved along a length of a vein of the patient beneath the skin of the patient. The vein-branch accessing device includes guiding means adapted for guiding the vein-branch accessing device along the vein until the vein-branch accessing device comes into a vicinity of a vein branch, and further includes an accessing apparatus adapted for accessing the vein branch of the vein. The guiding means may include either a vein bed separator or a vein guide. The vein-branch accessing device is adapted for being moved along the vein of the patient by a pressure exerted onto the vein-branch accessing device by a user. The vein-branch accessing device is adapted for being moved along a length of the vein, past the incision, under the skin of the patient.

According to another aspect of the present invention, a vein-branch accessing device includes a body having a first side, a second side, a proximal end, and a distal end. The vein-branch accessing device further includes a first access port disposed near the first side of the body and a second access port disposed near the second side of the body. Both the first access port and the second access port are adapted for accommodating a vein-branch tool therethrough. The vein-branch tool is adapted for performing at least one of a cutting operation and an occluding operation. The vein-branch accessing device further includes a vein guide, which is disposed on the body generally between the first access port and the second access port. The vein guide is adapted for guiding the vein-branch accessing device along the vein until the vein-branch accessing device reaches a vein branch. The first access port is adapted for facilitating access to vein branches on a first side of the vein, and the second access port is adapted for facilitating access to vein branches on a second side of the vein.

The vein-branch accessing device further includes a first alignment arm disposed near the first side of the body and a second alignment arm disposed near the second side of the body. The first access port includes a first axis and the second access port includes a second axis. The first axis and the second axis lie in a plane, with the vein guide being disposed on a first side of the plane and the first and second alignment arms being disposed on a second side of the plane. A proximal end of the vein guide is joined to the distal end of the body, and a distal end of the vein guide includes a shovel-shaped head.

The distal end of the vein guide may, alternatively, include a first probe and a second probe. The vein-branch accessing device may further include a first probe stop disposed on the first probe, a second probe stop disposed on the second probe, a first arm stop disposed on the first alignment arm, and a second arm stop disposed on the second alignment arm. The first probe stop may include a first transverse probe surface that is generally perpendicular to the first axis, and the second probe stop may include a second transverse probe surface that is generally perpendicular to the second axis. Additionally, the first arm stop may include a first transverse arm surface that is generally perpendicular to the first axis, and the second arm stop may include a second transverse arm surface that is generally perpendicular to the second axis. The first transverse probe surface, the second transverse probe surface, the first transverse arm surface, and the second transverse arm surface all lie generally in a second plane that is generally perpendicular to the plane having the first axis and the second axis. A volume between the first probe stop, the second probe stop, the first arm stop, and the second arm stop defines a working space of the vein-branch accessing device. The vein-branch accessing device further includes an auxiliary port disposed near the distal end of the body. The auxiliary port is adapted for accommodating a light, a scope, and an insufflation device.

According to yet another aspect of the present invention, a vein-branch accessing device includes a body having a first side, a second side, a proximal end, and a distal end. The vein-branch accessing device further includes a first access port disposed near the first side of the body, a second access port disposed near the second side of the body, and a shuttle assembly adapted for providing alternative access from an external line to either the first access port or the second access port. The vein-branch accessing device further includes a first switch box having both a first intermediate port and a second intermediate port. The first intermediate port is adapted for being connected to the first access port, and the second intermediate port is adapted for being connected to the second access port. The vein-branch accessing device further includes an intermediate line adapted for being connected to the external line and for being alternatively connected to either the first intermediate port or the second intermediate port.

The intermediate line is switchable between a first operating configuration and a second operating configuration. In the first operating configuration, the intermediate line is connected between the external line and the first intermediate port, and in the second operating configuration, the intermediate line is connected between the external line and the second intermediate port. The vein-branch accessing device further includes a second switch box disposed proximally of the first switch box. The first switch box slidably accommodates a distal line end of the intermediate line, and the second switch box slidably accommodates a proximal line end of the intermediate line. An intermediate auxiliary line is adapted for being connected between the auxiliary port, the first switch box, and the second switch box. The intermediate auxiliary line provides structural support between the first switch box and the second switch box, to thereby hold the second switch box in a stable orientation relative to the first switch box and, further, to facilitate smooth switching of the intermediate line between the first operating configuration and the second operating configuration.

According to a method of the present invention, a vein-branch accessing device is inserted through an incision in the skin of a patient. A vein guide of the vein-branch accessing device is then placed over a surface of the vein, and the vein-branch accessing device is moved along the surface of the vein in a distal direction, until the vein-branch accessing device comes into close proximity with the vein branch. A vein branch tool is then placed into contact with the vein branch, to thereby perform an operation on the vein branch. After the operation has been performed on the vein branch, the vein-branch accessing device is moved over the surface of the vein in a proximal direction. The vein branch tool may include either a vein-branch occluding device or a vein-branch severing device. After an operation has been performed on a first vein branch, the vein branch tool may be removed from a first passage of the vein-branch accessing device and inserted through a second passage of the vein-branch accessing device to thereby perform a second operation on a second vein branch. The vein-branch accessing device is not removed from the incision, during a period from the contacting of the first vein branch by the vein branch tool to the contacting of the second vein branch by the vein-branch tool.

The present invention, together with additional features and advantages thereof, may best be understood by reference to the following description taken in connection with the accompanying illustrative drawings.

BRIEF DESCRIPTION OF THE DRAWINGS

FIG. 1 illustrates a perspective view of the vein-branch accessing device according to a presently preferred embodiment of the present invention;

FIG. 2 illustrates an end view of the vein-occluding head of the vein-branch accessing device of the presently preferred embodiment;

FIG. 3 illustrates a cross-sectional view taken along line 3—3 of the vein-branch accessing device shown in FIG. 1;

FIG. 9 illustrates a second preferred embodiment of the vein-branch accessing device of the present invention;

FIG. 10 illustrates an end view of the vein harvesting head, taken along line 10—10 of FIG. 9;

FIG. 11 illustrates a side-elevational view of the vein-branch accessing device of the second preferred embodiment;

FIG. 12 illustrates an end view, taken along line 12—12, of the vein-branch accessing device of FIG. 11;

FIG. 13 illustrates a partial cross-sectional view of the vein-branch accessing device shown in FIG. 12;

FIG. 14 illustrates a side-elevational view of both the vein-branch accessing device of the second preferred embodiment and an occluded vein branch;

FIG. 15 illustrates a partially rotated orientation of the vein-branch accessing device of the second preferred embodiment;

FIG. 16 illustrates a top-planar view of the vein-branch accessing device of the second preferred embodiment, with a clip applier being applied to a side branch of a vein.

DETAILED DESCRIPTION OF THE PRESENTLY PREFERRED EMBODIMENT

Figure 4:
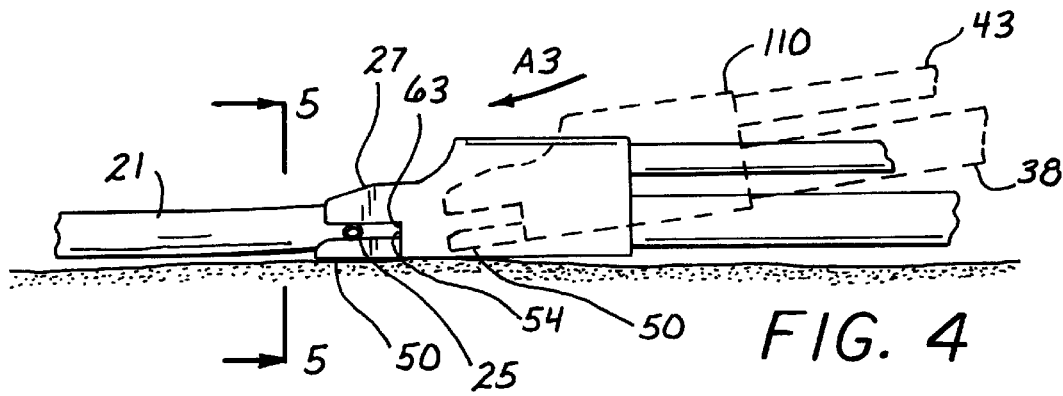
FIG. 4 illustrates a side-elevational view of the vein-branch accessing device of the presently preferred embodiment.

Turning to FIG. 1, a vein-branch accessing device 18 according to a presently preferred embodiment is shown next to a greater saphenous vein 21, which includes a first side branch 23 and a second side branch 25. The vein-branch accessing device 18 comprises a vein occluding head 27, a first switch box 30, and a second switch box 32. A first connecting line 34 connects the first switch box 30 to a first access port 36, and a second connecting line 38 connects the first switch 30 to a second access port 41 (FIG. 2). An intermediate auxiliary line 43 connects the first switch box 30 to an auxiliary port 45.

Both the first access port 36 and the second access port 41 of the vein occluding head 27 are adapted for accommodating vein-branch tools therethrough. The auxiliary port 45 is adapted for accommodating a vision fiber, a light fiber, and an insufflation line therethrough. The vision fiber attaches to an eye piece for a camera located outside of the operating area of the patient, and the light fiber attaches to a light post outside of the operating area of the patient. The vein branch tool can be inserted through either the first connecting line 34 or the second connecting line 38, and out of either the first access port 36 or the second access port 41, respectively. The intermediate auxiliary line 43 feeds the vision fiber, the light fiber, and the insufflation line to the auxiliary port 45. As presently embodied, the vision fiber provides an approximately 30 degree angle of view to the user of the vein-branch accessing device 18.

The vein occluding head 27 of the vein-branch accessing device 18 comprises a first probe 47 and a second probe 50. The first probe 47 and the second probe 50 together comprise a vein guide, which is adapted for fitting over the saphenous vein 21 and contacting opposing surfaces of the saphenous vein 21. When the inner surfaces of the first probe 47 and second probe 50 contact the opposing surfaces of the saphenous vein 21, the vein occluding head 27 can be guided along a length of the saphenous vein 21. As shown in FIG. 2, a curved surface 51 of the vein occluding head 27 is disposed between the first probe 47 and the second probe 50. The curved surface 51 provides another guiding surface for contacting the saphenous vein 21 when the vein occluding head 27 is moved along the length of the saphenous vein 21.

As presently embodied, the first probe 47 comprises a first transverse probe stop 52, and the second probe 50 comprises a second transverse probe stop 54. Since side branches of a greater saphenous vein generally tend to be located in the same plane, the first transverse probe stop 52 and the second transverse probe stop 54 are adapted for contacting most if not all of the side branches of any given saphenous vein. As shown in FIG. 1, the first transverse probe stop 52 will contact and align the first side branch 23, and the second transverse probe stop 54 will contact and align the second side branch 25. According to the presently preferred embodiment, the vein occluding head 27 further comprises a first alignment arm 56 and a second alignment arm 58. A working space of the vein occluding head 27 is defined between the first probe 47, the second probe 50, the first alignment arm 56, and the second alignment arm 58. The first alignment arm 56 comprises a first transverse arm stop 61, and the second alignment arm 58 comprises a second transverse arm stop 63. The first transverse arm stop 61 is adapted for contacting the first side branch 23, for example, generally when the first transverse probe stop 52 contacts the first side branch 23. Similarly, the second transverse arm stop 63 is adapted for contacting the second side branch 25, for example, generally when the second transverse probe stop 54 contacts the second side branch 25.

As presently embodied, the surfaces of both the first transverse probe stop 52 and the first transverse arm stop 61 are approximately perpendicular to an axis of the saphenous vein 21. Similarly, the surfaces of the second transverse probe stop 54 and the second alignment arm 58 are approximately perpendicular to the axis of the saphenous vein 21. Additionally, the surfaces of the first transverse probe stop 52 and the first transverse arm stop 61 are approximately perpendicular to an axis of the first access port 36, and the surfaces of the second transverse probe stop 54 and the second transverse arm stop 63 are approximately perpendicular to an axis of the second access port 41.

The first transverse probe stop 52 of the first probe 47 and the first transverse arm stop 61 of the first alignment arm 56 are both configured for contacting and aligning the first side branch 23 in front of the first access port 36. Both the first transverse probe stop 52 and the first transverse arm stop 61 are presently embodied to push in a distal direction against the first side branch 23, since the side branches of a saphenous vein are generally oriented in a proximal direction along the length of the saphenous vein. As shown in FIG. 1, the first side branch 23 and the second side branch 25 of the saphenous vein 21 are shown oriented slightly in the proximal direction.

Similarly to the first transverse probe stop 52 and the first transverse arm stop 61, the second transverse probe stop 54 and the second transverse arm stop 63 are designed to contact the second side branch 25 and to slightly push the second side branch 25 in the distal direction. Additionally, as with the first transverse probe stop 52 and the first transverse arm stop 61, the second transverse probe stop 54 and the second transverse arm stop 63 provide opposing lower and upper forces on the second side branch 25, respectively, to thereby align the second side branch 25 in front of the second access port 41.

The shuttle assembly 70 of the vein-branch accessing device 18 comprises the first switch box 30, the second switch box 32, the intermediate auxiliary line 43, and an intermediate line 72. The intermediate line 72 comprises a distal line end 74 and a proximal line end 76. A first adapter 78 (FIG. 3) is joined to the distal line end 74, and a second adapter (not shown) is joined to the proximal line end 76.

As illustrated in FIG. 3, the first adapter 78 fits around the distal line end 74, and comprises an upper protrusion 81 and a lower protrusion 83. The upper protrusion 81 of the first adapter 78 is adapted for sliding within an upper slot 85 of the first switch box 30 in the direction of either the arrow A1 or the arrow A2, and the lower protrusion 83 is adapted for sliding within a lower slot 87 within the first switch box 30 in the direction of either the arrow A1 or the arrow A2. Similarly, the second adapter has upper and lower protrusions, which are adapted for sliding within upper and lower slots of the second switch box 32.

As shown in FIG. 1, an external line 94 is integrally connected to the intermediate line 72 via the second switch box 32. The intermediate auxiliary line 43 passes through both the second switch box 32, the first switch box 30, and into the vein occluding head 27. This intermediate auxiliary line 43 adds rigidity to the first switch box 30 and the second switch box 32, to thereby hold the two boxes 30, 32 in a relatively stable orientation relative to one another. In an alternative embodiment, the external line 94 is not used, and/or the intermediate auxiliary line 43 terminates at the second switch box 32.

As shown in FIG. 3, the upper slot 85 is located directly above the lower slot 87, to thereby facilitate movement of the first adapter 78 in the direction of the arrow A2. Movement of the first adapter 78 from a first intermediate port 101 to a second intermediate port 103 of the first switch 30 results in a disconnection of the intermediate line 72 from the first connecting line 34 and a connection of the intermediate line 72 with the second connecting line 38. Access to the first access port 36 and the second access port 41 can thus be provided alternately by the shuttle assembly 70. For example, a vein branch tool may first be inserted throughout the intermediate line 72, the second connecting line 38 and out of the second access port 41 to thereby perform a first operation on the second side branch 25, and then removed from the second connecting line 38. The intermediate line 72 can then be moved from the second intermediate port 103 to the first intermediate port 101, and the vein branch tool can be inserted through the first connecting line 34 and out of the first access port 36 to thereby facilitate an operation on the first side branch 23.

As the intermediate line 72 is switched between a first configuration providing access to the first connecting line 34 and a second configuration providing access to the second connecting line 38, the intermediate auxiliary line 43 provides structural support between the first switch box 30 and the second switch box 32, to thereby facilitate smooth switching of the intermediate line 72 between the two operating configurations.

FIG. 4 illustrates a first insertion position 110 of the vein-branch accessing device 18, after the vein-branch accessing device 18 is inserted through an incision in the skin of a patient. The first probe 47 and the second probe 50 are placed on opposing sides of the saphenous vein 21, so that the vein occluding head 27 straddles the saphenous vein 21. A general movement of the vein-branch accessing device 18 in the direction of the arrow A3 facilitates this action, and also moves the first probe 47 and the second probe 50 along the vein bed 114 until the second side branch 25 is just distal of the second probe 50.

Figure 5:
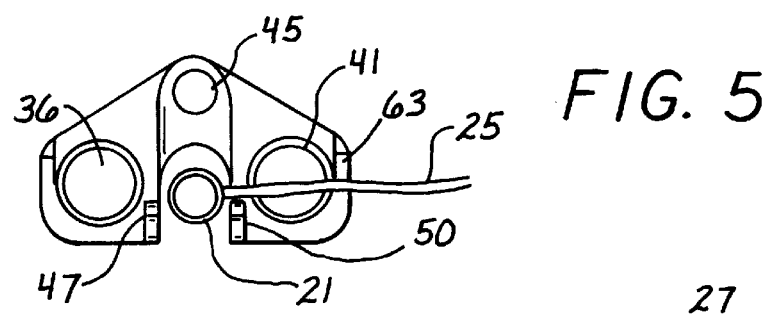
FIG. 5 illustrates a front end view, taken along line 5—5, of the vein-branch accessing device of FIG. 4.
Figure 6:
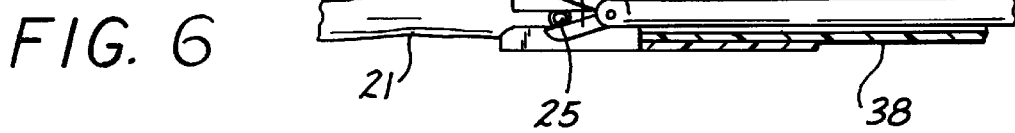
FIG. 6 illustrates a partial cross-sectional view of the vein-branch accessing device shown in FIG. 4.

The second probe 50 has a sloped distal end adapted for fitting between the side branch 25 and the vein bed 114. The second probe 50 is thus capable of efficiently separating the second side branch 25 from the vein bed 114. Next, the vein-branch accessing device 18 is moved further in a distal direction by the hand of a user, for example, until the second transverse probe stop 54 and the second transverse arm stop 63 contact the second side branch 25. These two stops 54, 63 serve to align the second side branch 25 across the second access port 41. A vein branch tool, such as a clip applier, may then be inserted through the second access port 41 to place a clip around the second side branch 25 and ligate the second side branch 25. FIG. 5 illustrates the alignment of the second side branch 25 across the second access port 41, and FIG. 6 illustrates a partial cross-sectional view where a clip 121 of a clip applier 123 is being applied around the second side branch 25.

Figure 7:
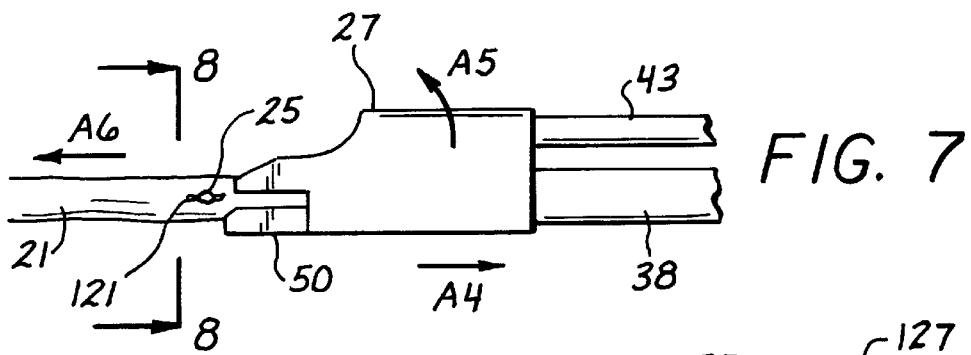
FIG. 7 illustrates a side-elevational view of both the vein-branch accessing device of the presently preferred embodiment and an occluded vein branch.
Figure 8:
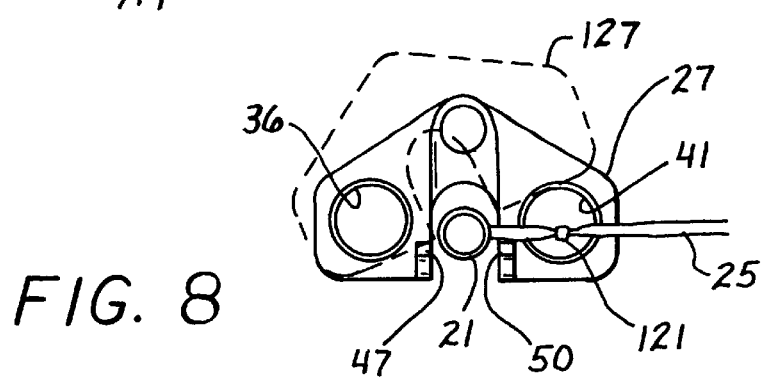
FIG. 8 illustrates a partially rotated orientation of the vein-branch accessing device of the presently preferred embodiment.

After the second side branch 25 is ligated, the vein-branch accessing device 18 is moved proximally in the direction of the arrow A4, as illustrated in FIG. 7. The vein-branch accessing device 18 is then rotated about an axis of the saphenous vein 21 in the direction of the arrow A5. FIG. 8 illustrates the rotated advancement position 127 of the vein-branch accessing device 18. When the vein-branch accessing device 18 is moved to the rotated advancement position 127, the vein-branch accessing device 18 can be moved distally along the saphenous vein 21 to another side branch, without disturbing the ligated side branch 25.

FIGS. 9–16 illustrate a second preferred embodiment of the present invention, where similar parts are labeled with like reference numerals. A major difference between the second embodiment and the first embodiment of the present invention lies in the shape of the vein guide. The vein guide of the first embodiment comprises a first probe 47 and a second probe 50, whereas the vein guide of the second embodiment comprises a vein bed separator 130. This second preferred embodiment of the present invention is adapted for harvesting a greater saphenous vein 21, which involves severing the side branches from the saphenous vein 21. Accordingly, clippers are used in addition to clips, to thereby perform the function of severing the side branches from the saphenous vein 21.

The saphenous vein 21 must be completely separated from the vein bed 114. A shovel-shaped tip 134 is provided at a distal end of the vein bed separator 130 for achieving this end. Of course, other surfaces suitable for separating the saphenous vein 21 from a vein bed may also be used. As shown in FIG. 10, an optional insertion passage 136 is provided in the vein harvesting head 138. Since the saphenous vein 21 is to be completely removed from the patient, a proximal end of this saphenous vein 21 is preferably first severed, before the saphenous vein 21 is inserted through the insertion passage 136. The saphenous vein 21 is then aligned along the vein bed separator 130, within the generally circular area 140 shown in FIG. 10. The vein harvesting head 138 is thus adapted to completely surround the saphenous vein 21, to therefore act as both a vein guide and a vein bed separator.

As shown in FIG. 11, the vein harvesting head 138 of the vein-branch accessing device 18 is inserted through an incision of the patient and moved to the second side branch in a manner similar to that described above with reference to the first embodiment of the present invention. When the saphenous vein 21 is to be harvested, however, the proximal end of the saphenous vein 21 is preferably first cut, and the proximal portion of the saphenous vein 21 is place through the insertion passage 136 before the vein harvesting head 138 is moved from the first insertion position 136 in the direction of the arrow A7 to the second insertion position 138. By the time that the second side branch 25 is aligned by the parallel, horizontal surfaces of the vein bed separator 130, the first transverse arm stop 61, and the second transverse arm stop 63, the proximal portion of the saphenous vein 21 up to this second side branch 25 is severed from the vein bed 114.

FIG. 12 shows the positioning of the saphenous vein 21 and the second side branch 25 within the vein harvesting head 138, and FIG. 13 shows a partial cross-sectional view with a clipper applier 143 and a clipper 145 placed within the second connecting line 38 and through the second access port 41. Before the clipper 145 is used to sever the second side branch 25 from the saphenous vein 21, a clip 121 (FIG. 6) is preferably first applied around the second side branch 25. FIG. 14 shows the clip 121 applied around the remaining portion of the severed second side branch 25.

When the side branches are severed from the saphenous vein 21, the vein harvesting head 138 does not necessarily need to be rotated before advancement in the distal direction to another side branch. An operator may choose, however, to first move the vein harvesting head 138 in the direction the arrow A8 and to subsequently rotate the vein harvesting head 138 in the direction of arrow A9, before advancing the vein harvesting head 138 to another side branch. FIG. 15 shows a rotated advancement position 150 of the vein harvesting head 138. This optional rotated advancement position 150 allows a ligated and severed side branch to pass through the optional insertion passage 136. Alternatively, if an operator chooses not to sever a side branch 25, then the rotated advancement position 150 may be used in order to advance the vein harvesting head 138 to another side branch. FIG. 16 shows a top planar view where a clip applier 123 is used to apply a clip 121 onto a saphenous vein side branch 25. After the clip 121 is applied to the side branch 25, the remaining side branch is severed from the saphenous vein 21. Severing may require removal of the clip applier 123 and insertion of a vein cutter (not shown) into the intermediate line 72. After the vein cutter is used, the vein cutter is removed from the second connecting line 38 and, subsequently, the intermediate line 72 is moved into alignment with the first connecting line 34. The vein harvesting head 138 is then moved to the first side branch 23, and the clip applier 123 is inserted through the first connecting line 34 with a new clip 121. The new clip 121 is then inserted around the side branch 23, before the side branch 23 is severed from the saphenous vein 21.

Although an exemplary embodiment of the invention has been shown and described, many other changes, modifications and substitutions, in addition to those set forth in the above paragraphs, may be made by one having ordinary skill in the art without necessarily departing from the spirit and scope of this invention.

What is claims is:

1. A vein-branch accessing device for accessing vein branches of a vein, the vein-branch accessing device having an elongate configuration with a proximal end and a distal end, comprising:
    a vein-occluding head disposed at the distal end of the device;
    at least one probe included in the occluding head and adapted for contacting a surface of the vein and for moving along the surface of the vein, to thereby guide the vein-branch accessing device over the surface of the vein;
    a vein branch indicator included in the occluding head and adapted for indicating to an operator of the vein-branch accessing device that the probe has moved along the surface of the vein to a vein branch of the vein; and
    portions of the occluding head defining at least one port facilitating access to the vein branch of the vein.

2. The vein-branch accessing device as recited in claim 1, wherein the port is sized and configured to receive a clip therethrough for occluding the vein branch.

3. The vein-branch accessing device as recited in claim 1, wherein the port is sized and configured to receive a cutter therethrough for severing the vein branch from the vein.

4. The vein-branch accessing device as recited in claim 3, the at least one probe comprising a vein bed separator.

5. The vein-branch accessing device as recited in claim 1, the vein branch indicator comprising a transverse surface of the at least one probe.

6. The vein-branch accessing device as recited in claim 1, the at least one probe being adapted for contacting and moving along the surface of the vein, insitu.

7. A vein-branch accessing device for accessing vein branches of a vein, the vein-branch accessing device, comprising:
    at least one probe adapted for contacting a surface of the vein and for moving along the surface of the vein, to thereby guide the vein-branch accessing device over the surface of the vein;
    a vein branch indicator adapted for indicating to an operator of the vein-branch accessing device that the probe has moved along the surface of the vein to a vein branch of the vein;
    accessing means adapted for facilitating access to the vein branch of the vein, the accessing means being sized and configured to receive a cutter therethrough, the cutter being adapted for severing the vein branch from the vein; and
    the at least one probe including a vein bed separator comprising a shovel-shaped blade.

8. A vein-branch accessing device for accessing vein branches of a vein, the vein-branch accessing device, comprising:
    at least one probe adapted for contacting a surface of the vein and for moving along the surface of the vein, to thereby guide the vein-branch accessing device over the surface of the vein;
    a vein branch indicator adapted for indicating to an operator of the vein-branch accessing device that the probe has moved along the surface of the vein to a vein branch of the vein;
    accessing means adapted for facilitating access to the vein branch of the vein, the accessing means being sized and configured to receive a cutter therethrough for severing the vein branch from the vein; and
    the vein branch indicator comprising a scope.

9. A vein-branch accessing device moveable along a vein of a patient to access a first vein branch on one side of the vein and a second vein branch on another side of the vein, the vein-branch accessing device having an elongate configuration with a proximal end and a distal end, comprising:
    a head disposed at the distal end of the device;
    a guide included in the head and being adapted for guiding the vein-branch accessing device along the vein
    first portions of the head defining a first access port moveable into proximity with the first vein branch on the one side of the vein;
    second portions of the head defining a second access port moveable into proximity with the second vein branch on the other side of the vein; and
    an accessing apparatus insertable through one of the first port and second port to access the associated first vein branch and second vein branch.

10. The vein-branch accessing device as recited in claim 9, the accessing apparatus comprising a port adapted for accommodating a ligating clip therethrough, the clip being adapted for occluding the vein branch.

11. The vein-branch accessing device as recited in claim 9, the accessing apparatus comprising a port adapted for accommodating a cutter for severing the vein branch outwardly of the vein.

12. The vein-branch accessing device as recited in claim 11, the guide comprising a vein bed separator.

13. The vein-branch accessing device recited in claim 9, further comprising:
    a switch box having a fixed relationship with the head and defining a third port communicating with the first port of the head and a fourth port communicating with the second port of the head;
    an access tube adapted to receive the accessing apparatus and extending from the proximal end of the device to the switch box;
    the tube being moveable between a first position and a second position;
    the tube in the first position communicating with the third port of the box and the first port of the head to provide access for the apparatus to the first vein branch; and
    the tube in the second position communicating with the fourth port of the box and the second port of the head to provide access for the apparatus to the second vein branch.

14. A vein-branch accessing device adapted to be inserted through an incision of the skin of a patient and to be moved along a vein of the patient beneath the skin, the vein-branch accessing the device comprising:

guide means adapted for guiding the vein-branch accessing device along the vein until the vein-branch accessing device comes into proximity with a vein branch;

an accessing apparatus adapted for accessing a vein branch of the vein, the apparatus having a port adapted for accommodating a clip applier therethrough, the clip applier having characteristics for severing the vein branch from the vein; and the guide means including a vein bed separator comprising a shovel-shaped blade.

15. The vein-branch accessing device as recited in claim 14, the guide means comprising a vein guide.

16. The vein branch accessing device as recited in claim 15, the guide means comprising a scope.

17. The vein-branch accessing device as recited in claim 16, wherein the vein-branch accessing device is adapted for being moved along the vein of the patient by pressure exerted on the vein-branch accessing device by a user.

18. The vein-branch accessing device as recited in claim 17, wherein the vein-branch accessing device is adapted for being inserted through an incision in the skin of the patient and, subsequently, for being moved along the length of the vein, past the incision, under the skin of the patient.

19. A vein-branch accessing device for accessing first and second vein branches of a vein, the vein-branch accessing device comprising:

a body having a first side, a second side, a proximal end, and a distal end;

first portions of the body defining a first access port in proximity to the first side of the body, the first access port being adapted to operatively receive a vein branch tool for performing at least one operation on the first vein branch;

second portions of the body defining a second access port in proximity to the second side of the body, the second access port being adapted to operatively receive a vein branch tool for performing at least one operation on the second vein branch; and a vein guide disposed on the body generally between the first access port and the second access port, the vein guide being adapted for guiding the vein-branch accessing device along the vein into proximity with the vein branch.

20. The vein-branch accessing device as recited in claim 19, the first access port being positioned relative to the guide for facilitating access to the first vein branch on a first side of the vein, and the second access port being positioned relative to the guide for facilitating access to the second vein branch on a second side of the vein.

21. The vein-branch accessing device as recited in claim 20, further comprising:

a first alignment arm disposed on the first side of the body; and a second alignment arm disposed on the second side of the body.

22. The vein-branch accessing device as recited in claim 21, wherein:

the first access port has a first axis, the second access port has a second axis, and both the first axis and the second axis are disposed generally in a first plane;

the vein guide is disposed on a first side of the first plane; and the first alignment arm and the second alignment arm are disposed on a second side of the first plane.

23. The vein-branch accessing device as recited in claim 22, the vein guide comprises:

a proximal end joined to the distal end of the body; and a distal end with a shovel-shaped head.

24. The vein-branch accessing device as recited in claim 22, the vein guide comprising a first probe and a second probe.

25. The vein-branch accessing device as recited in claim 24, further comprising:

a first probe stop disposed on the first probe;

a second probe stop disposed on the second probe;

a first arm stop disposed on the first alignment arm; and a second arm stop disposed on the second alignment arm.

26. The vein-branch accessing device as recited in claim 25, further comprising:

the first probe stop including a first transverse probe surface which is generally perpendicular to the first axis;

the second probe stop including a second transverse probe surface which is generally perpendicular to the second axis;

the first arm stop including a first transverse arm surface which is generally perpendicular to the first axis; and the second arm stop including a second transverse arm surface which is generally perpendicular to the second axis.

27. The vein-branch accessing device as recited in claim 26, the first transverse probe surface, the second transverse probe surface, the first transverse arm surface, and the second transverse arm surface being disposed generally in a second plane.

28. The vein-branch accessing device as recited in claim 27, a wherein the first probe stop, the second probe stop, the first arm stop, and the second arm stop defining a working space of the vein-branch accessing device.

29. The vein-branch accessing device as recited in claim 28, further comprising an auxiliary port disposed near the distal end of the body, the auxiliary port being adapted for accommodating at least one of a light, a sufflation device, and a scope.

30. The vein-branch accessing device as recited in claim 29, the auxiliary port being disposed on the second side of the first plane generally between the first access port and the second access port.

31. A vein-branch accessing device for accessing vein branches of a vein, the vein-branch accessing device comprising:

a body having a first side, a second side, a proximal end, and a distal end;

a first access port disposed near the first side of the body, the first access port being adapted for accommodating a vein branch tool therethrough;

a second access port disposed near the second side of the body, the second access port being adapted for accommodating a vein branch tool therethrough; and a shuttle assembly moveable relative to the body and adapted for providing alternative communication between an external line and one of the first access port and the second access port.

32. The vein-branch accessing device as recited in claim 31, the shuttle assembly comprising:

a first switch box having a first intermediate port and a second intermediate port, the first intermediate port communicating with the first access port and the second intermediate port communicating with the second access port; and an intermediate line adapted for alternative connection to one of the first intermediate port and the second intermediate port.

33. The vein-branch accessing device as recited in claim 32, the intermediate line being switchable relative to the first switch box between a first operating configuration and a second operating configuration, the intermediate line connecting the external line to the first intermediate port in the first operating configuration, and the intermediate line connecting the external line to the second intermediate port in the second operating configuration.

34. The vein-branch accessing device as recited in claim 33, the intermediate line comprising a proximal line end and a distal line end, the shuttle assembly comprising a second switch box disposed proximally of the first switch box, and the first switch box slidably accommodating the distal line end and the second switch box slidably accommodating the proximal line end.

35. The vein-branch accessing device as recited in claim 34, further comprising an auxiliary port disposed near the distal end of the body, the auxiliary port being adapted for accommodating at least one of a light, an insufflation device, and a scope.

36. The vein-branch accessing device as recited in claim 35, the auxiliary port being disposed generally between the first access port and the second access port, and the shuttle assembly further comprising an intermediate auxiliary line adapted for being connected to the auxiliary port, and further being adapted for being connected to both the first switch box and the second switch box.

37. The vein-branch accessing device as recited in claim 36, the intermediate auxiliary line providing structural support between the first switch box and the second switch box, to thereby hold the second switch box in a stable orientation relative to the first switch box, and to facilitate switching the intermediate line between the first operating configuration and the second operating configuration.

38. The vein-branch accessing device as recited in claim 37, further comprising a vein guide disposed relative to the body and adapted for contacting a surface of the vein.

39. The vein-branch accessing device as recited in claim 38, the vein guide comprising a shovel-shaped blade.

40. The vein-branch accessing device as recited in claim 38, the vein guide comprising two probes.

41. The vein-branch accessing device as recited in claim 40, each of the two probes extending in a direction which is generally parallel to a line passing through a center of the body from the proximal end of the body to the distal end of the body, and each of the two probes being integrally formed with the body of vein-branch accessing device.

42. A vein-branch occluding device for occluding vein branches of a vein, the vein-branch occluding device comprising:

a body having a proximal end and a distal end;

two access ports disposed in the body;

two probes disposed on the body at the distal end of the body, the two probes being adapted for contacting a surface of a vein and for guiding the vein-branch occluding device along the surface of the vein; and two alignment arms disposed near the distal end of the body, the alignment arms being adapted for contacting the vein branches of the vein in order to facilitate stabilization of the vein branches relative to the vein-branch occluding device.

43. The vein-branch occluding device as recited in claim 42, each of the two probes also being adapted for contacting a vein branch in order to facilitate stabilization of the vein branches relative to the vein-branch accessing device.

44. The vein-branch occluding device as recited in claim 43, further comprising portions of the body defining an auxiliary port adapted for accommodating at least one of a light, an insufflation device, and a scope.

45. The vein-branch occluding device as recited in claim 44, further comprising a shuttle assembly adapted for providing alternative access from an external line to one of the two access ports.

46. The vein-branch occluding device as recited in claim 42, each of the two probes extending in a direction which is generally parallel to a line passing through a center of the body from the proximal end of the body to the distal end of the body.

47. A vein-branch harvesting device for severing vein branches from a vein, the vein-branch harvesting device comprising:

a body having two access ports, a proximal end, and a distal end;

a vein bed separator disposed on the body at the distal end of the body, the vein bed separator being adapted for contacting a surface of the vein and for separating the vein from a vein bed; and two alignment arms disposed near the distal end of the body, the two alignment arms being adapted for contacting the vein branches of the vein to facilitate stabilization of the vein branches relative to the vein-branch harvesting device.

48. A method of accessing at least one vein branch of a vein, comprising the following steps:

inserting a vein-branch accessing device through an incision in a patient;

placing a vein guide of the vein-branch accessing device onto a surface of the vein;

moving the vein-branch accessing device along the surface of the vein in a distal direction, until the vein-branch accessing device comes into close proximity with a vein branch; and contacting the vein branch with a vein branch tool of the vein-branch accessing device, to thereby perform an operation on the vein branch.

49. The method according to claim 48, further comprising the following steps:

moving the vein-branch accessing device over the surface of the vein in a proximal direction; and moving the vein-branch accessing device out of contact with the surface of the vein and out of the incision of the patient.

50. The method according to claim 48, the step of contacting the vein branch comprising a substep of contacting the vein with a vein-branch occluding device, to thereby occlude the vein branch.

51. The method according to claim 48, the step of contacting the vein branch comprising a substep of contacting the vein with a vein-branch severing device, to thereby sever the vein branch from the vein.

52. The method according to claim 48, the step of contacting the vein branch being preceded by a step of feeding the vein branch tool through a first passage of the vein-branch accessing device.

53. The method according to claim 52, the step of contacting the vein branch being followed by the following steps:

retracting the vein branch tool from the first passage of the vein-branch accessing device;

feeding the vein branch tool through a second passage of the vein-branch accessing device; and contacting a second vein branch with the vein branch tool, to thereby perform an operation on the second vein branch.

54. The method according to claim 53, wherein the vein-branch accessing device is not removed from the incision, during a period from the contacting of the first vein branch to the contacting of the second vein branch.

55. The method according to claim 54, the vein comprising a greater saphenous vein.

56. A method of performing a surgical function on at least one vein branch of a vein, comprising the following steps:

inserting a vein-branch accessing device through an incision in a patient, the device including a vein guide and at least one passage;

placing the vein guide of the vein-branch accessing device onto a surface of the vein;

moving the vein-branch accessing device along the surface of the vein until the vein-branch accessing device comes into close proximity with the one vein branch; and inserting a vein branch tool through the passage of the vein-branch accessing device to perform the surgical operation on the vein branch.

57. The method according to claim 56, the step of inserting the tool comprises the substeps of contacting the vein with a vein-branch occluding device, and occluding the vein branch.

58. The method according to claim 56, the step of inserting the tool comprises the substeps of contacting the vein with a vein-branch severing device, and severing the vein branch from the vein.

59. The method according to claim 56, the step of inserting the tool being preceded by a step of feeding the vein branch tool through the one passage of the vein-branch accessing device.

60. The method according to claim 56, the step of inserting the tool being followed by the following steps:

retracting the vein branch tool from the one passage of the vein-branch accessing device;

feeding the vein branch tool through a second passage of the vein-branch accessing device; and contacting a second vein branch with the vein branch tool to perform the surgical operation on the second vein branch.

61. The method according to claim 60, wherein the vein-branch accessing device remains in the incision during a period beginning with the first contacting step and ending with the second contacting step.

62. The method for operating an access device relative to a vein having a first vein branch and a second vein branch, including the steps of:

providing the access device with a body having a first port for accessing the first vein branch and a second port for accessing the second vein branch, and a shuttle having a single access tube moveable relative to the body between a first position and a second position;

guiding the body of the access device along the vein into proximity with the vein branch;

moving the shuttle to the first position to bring the access tube into communication with the first port; and inserting a tool through the access tube and the first port to access the first vein branch.

63. The method recited in claim 62, further comprising the steps of:

guiding the body of the access device along the vein and into proximity with the second vein branch;

moving the shuttle to the second position to bring the access tube into communication with the second port; and inserting the tool through the access tube and the second port to access the second vein branch.

64. The method recited in claim 62, wherein the guiding step includes the steps of:

providing the body with a pair of guide arms;

positioning the guide arms to engage different sides of the vein; and pushing the access device so as to slide the guide arms along the vein.

65. The method recited in claim 62 further comprising the steps of:

prior to the moving step inserting the access device through an incision;

maintaining the access device in the incision between the two inserting steps; and subsequent to the second inserting step, removing the access device from the incision.

* * * * *

UNITED STATES PATENT AND TRADEMARK OFFICE
CERTIFICATE OF CORRECTION

PATENT NO. : 5,814,059
DATED : September 29, 1998
INVENTOR(S) : Charles C. Hart, et. al.

It is certified that error appears in the above-identified patent and that said Letters Patent is hereby corrected as shown below:

Title page, item [56], under "References Cited, after line 4, insert--
5,667,480    9/1997   Knight    600/210--; and Title page, item [56], under References Cited, after line 5, insert --
5,725,479    3/1998   Knight    600/210--.

Signed and Sealed this

Twelfth Day of January, 1999

Attest:

Attesting Officer

Acting Commissioner of Patents and Trademarks